(12) United States Patent
Shimoyama et al.

(10) Patent No.: US 9,250,210 B2
(45) Date of Patent: Feb. 2, 2016

(54) GAS SENSOR

(71) Applicants: The University of Tokyo, Tokyo (JP); OMRON Corporation, Kyoto-shi (JP)

(72) Inventors: Isao Shimoyama, Tokyo (JP); Kiyoshi Matsumoto, Tokyo (JP); Yusuke Takei, Tokyo (JP); Hidetoshi Takahashi, Tokyo (JP); Noboru Kiga, Tokyo (JP); Masahito Honda, Tokyo (JP)

(73) Assignees: The University of Tokyo, Tokyo (JP); Omron Corporation, Kyoto-shi (JP)

( * ) Notice: Subject to any disclaimer, the term of this patent is extended or adjusted under 35 U.S.C. 154(b) by 41 days.

(21) Appl. No.: 14/366,912

(22) PCT Filed: Dec. 27, 2012

(86) PCT No.: PCT/JP2012/083879
§ 371 (c)(1),
(2) Date: Jun. 19, 2014

(87) PCT Pub. No.: WO2013/105449
PCT Pub. Date: Jul. 18, 2013

(65) Prior Publication Data
US 2014/0346042 A1    Nov. 27, 2014

(30) Foreign Application Priority Data
Jan. 13, 2012 (JP) .................................. 2012-004963

(51) Int. Cl.
*G01N 27/414* (2006.01)
*G01N 27/48* (2006.01)
(Continued)

(52) U.S. Cl.
CPC ............ *G01N 27/48* (2013.01); *G01N 27/4141* (2013.01); *G01N 27/4146* (2013.01);
(Continued)

(58) Field of Classification Search
CPC ........................ G01N 27/4141; G01N 27/4146
See application file for complete search history.

(56) References Cited

U.S. PATENT DOCUMENTS

| 2007/0048181 A1* | 3/2007 | Chang .................... B82Y 15/00 422/400 |
| 2007/0132043 A1 | 6/2007 | Bradley et al. |
| 2009/0008629 A1 | 1/2009 | Matsumoto et al. |

FOREIGN PATENT DOCUMENTS

| JP | 62-123348 S | 6/1987 |
| JP | H02138857 A | 5/1990 |

(Continued)

OTHER PUBLICATIONS

Bradley et al., "Charge Transfer from Ammonia Physiorbed on Nanotubes," Physical Review Letters vol. 91, No. 21, pp. 218301-1 to 218301-4.*

(Continued)

*Primary Examiner* — Alexander Noguerola
(74) *Attorney, Agent, or Firm* — Locke Lord LLP

(57) ABSTRACT

A gas sensor that can enhance gas detection sensitivity more than the conventional sensors with a simple configuration is proposed. An electric double layer including a gate insulating layer is formed in an ionic liquid (IL), a change of a state of the gate insulating layer in the ionic liquid (IL) that occurs by absorbing a gas is directly reflected in a source-drain current ($I_{sd}$) that flows in a carbon nanotube (8). Therefore, the gas detection sensitivity can be enhanced more than in the conventional sensors. Further, since the ionic liquid (IL) can be simply provided on a substrate (2) to be in contact with the carbon nanotube (8) and a gate electrode (7), the configuration that chemically modifies a surface of the carbon nanotube with a plurality of polymers as in the conventional gas sensors is not needed, and the configuration can be simplified correspondingly.

5 Claims, 17 Drawing Sheets

(51) Int. Cl.
  *G01N 33/00* (2006.01)
  *H01L 51/00* (2006.01)
  *H01L 51/05* (2006.01)

(52) U.S. Cl.
  CPC .......... *G01N33/004* (2013.01); *G01N 33/0054* (2013.01); *H01L 51/0048* (2013.01); *H01L 51/0508* (2013.01)

(56) References Cited

FOREIGN PATENT DOCUMENTS

| JP | H03237350 A | 10/1991 | |
|---|---|---|---|
| JP | 04000223 B2 * | 1/1992 | ........... G01N 27/414 |
| JP | 06079009 B2 * | 10/1994 | ........... G01N 27/414 |
| JP | 2004085392 A | 3/2004 | |
| JP | 2006222279 A | 8/2006 | |
| JP | 2007505323 A | 3/2007 | |
| JP | 2010192599 | 9/2010 | |
| JP | 2010197181 A | 9/2010 | |
| JP | 2010203838 A | 9/2010 | |
| JP | 2010261793 A | 11/2010 | |
| WO | WO-2011155179 A1 | 12/2011 | |

OTHER PUBLICATIONS

Bradley et al., "Influence of Mobile Ions on Nanotube Based FET Devices," Nano Letters 2003 vol. 3, No. 5, pp. 639-641.*
JPO computer-generated English language translation of JP 2006-222279 A, downloaded Sep. 23, 2015.*
JPO computer-generated English language translation of JP H06-079009 B2, downloaded Sep. 23, 2015.*
International Search Report issued in PCT/JP2012/083880, dated Jan. 29, 2013.
S. Miwa et al., "Selective gas detection by means of surface plasmon responance sensors," Thin Solid Films 281-282, 446-468, (1996).
S. Neethirajan et al., "Carbon Dioxide ($CO_2$) Sensors for the Agri-food Industry—A Review," Food Bioprocess Technol. 2:p. 115-121, (2009).
A. Star et al., "Nanoelectronic $CO_2$ breath sensors", NSTI Nanotech 2005, vol. 1, 2005, pp. 104-107.
Keat G. Ong et al., "A Carbon Nanotube-based Sensor for $CO_2$ Monitoring", Sensors 2001, vol. 1, 2001, pp. 193-205.
Iddo Heller et al., "Influence of Electrolyte Composition on Liquid-Gated Carbon Nanotube and Graphene Transistors", Journal of the American Chemical Society, vol. 132, 2010, pp. 17149-17156.
N. Kiga et al., "CNT-FET gas sensor using a functionalized ionic liquid as gate", Micro Electro Mechanical Systems(MEMS), 2012 IEEE 25th International Conference on, Jan. 29, 2012, pp. 796-799.
Supplementary European Search Report dated Jul. 15, 2015, issued for the Europena patent application No. 12864780.7.
K. Ishizu et al., "Carbon Dioxide Detection by Surface Plasmon Resonance with Ionic Liquid," The University of Tokyo, 978-1-4673-0324-8/12, 784-787, (2012).
N. Kiga et al. "CNT-FET Gas Sensor Using a Multifunctionalized Ionic Liquid as Gate, " The University of Tokyo, 978-1-4673-0324-8/12, 796-799, (2012).
A. Star et al., "Nanoelectronic Carbon Dioxide Sensors," Advanced Materials 16, No. 22, 2049-2052, (2004).
International Search Report issued in PCT/JP2012/083879, dated Apr. 2, 2013.

* cited by examiner

GAS SENSOR

CROSS REFERENCE TO RELATED APPLICATIONS

This application is a U.S. National Stage application under 35 U.S.C. §371 of International Patent Application Serial No. PCT/JP2012/083879, filed Dec. 27, 2012, which Application claims the benefit of priority of Japanese Patent Application No. JP2012-004963, filed Jan. 13, 2012, the disclosures of each of which are expressly incorporated by reference in their entireties. This application is also related to a U.S. National Stage application under 35 U.S.C. §371 of International Patent Application Serial No. PCT/JP2012/083880, filed Dec. 27, 2012, which Application claims the benefit of priority of Japanese Patent Application No. JP2012-004964, filed Jan. 13, 2012, the disclosures of each of which are expressly incorporated by reference in their entireties, which was entered into U.S. on Jun. 24, 2014.

TECHNICAL FIELD

The present invention relates to a gas sensor, and is suitable to be applied to detection of, for example, gases such as $CO_2$ and $NH_3$.

BACKGROUND ART

In recent years, studies on gas sensors capable of detecting various gases such as $CO_2$ and $NH_3$ have been conducted, and among them, gas sensors using carbon nanotubes (CNTs), for example, have been especially attracting attention from the viewpoint of detection sensitivity for gases, miniaturization, and energy saving (for example, see Patent Literature 1 and Non Patent Literature 1). In fact, the gas sensor using a carbon nanotube like this has a configuration in which the surfaces of the carbon nanotube provided between a source electrode and a drain electrode are chemically modified with two kinds of polymers, in order to detect $CO_2$ that is a target of detection, for example. Further, the gas sensor is configured in such a manner that the carbon nanotube is disposed on the silicon back gate via a silicon oxide film, and a gate voltage can be applied to the silicon back gate.

CITATION LIST

Patent Literature

Patent Literature 1: National Publication of International Patent Application No. 2007-505323

Non Patent Literature

Non Patent Literature 1: A. Star, T. R. Han, V. Joshi, J. C. P. Gabriel, G. Gruner, "Nanoelectronic Carbon Dioxide Sensors", Advanced Materials, Vol. 16, No. 22, 2004.

SUMMARY OF INVENTION

Technical Problem

However, in order to enable the gas sensor configured as above to detect $CO_2$ by using a carbon nanotube, surface chemical modification of the carbon nanotube needs to be performed by two kinds of polymers, and therefore, there arises the problem that the configuration is complicated correspondingly. Further, while the gas sensor like this can detect a gas that is a target of detection, enhancement in detection sensitivity is desired so that the gas sensor can detect an extremely small quantity of gas.

Consequently, the present invention has been made with the above respects taken into consideration. An object of the present invention is to propose a gas sensor capable of enhancing gas detection sensitivity more than the conventional gas sensors, with a simple configuration.

Solution to Problem

A first aspect of the present invention is a gas sensor that detects a gas that is a target of detection, the gas sensor includes: a carbon nanotube provided between a source electrode and a drain electrode on a substrate, and a source-drain current flows therein; and a gas absorbing liquid disposed to cover the carbon nanotube, and is featured in that the gas is detected based on a change of the source-drain current in the carbon nanotube caused by absorbing the gas in the gas absorbing liquid.

Further, a second aspect of the present invention is the gas sensor, wherein the gas absorbing liquid is in contact with the carbon nanotube and a gate electrode on the substrate to become a gate insulating layer, a state of the gate insulating layer changes by absorbing the gas, and the gas is detected based on a change of the source-drain current that occurs in response to the state of the gate insulating layer.

Advantageous Effect of Invention

According to the first aspect of the present invention, the change of the state of the electric charges in the gas absorbing liquid, which occurs by absorption of a gas is directly reflected in the source-drain current that flows in the carbon nanotube, and therefore, gas detection sensitivity can be enhanced more than the conventional gas sensors. Further, since surface chemical modification does not have to be performed for the carbon nanotube itself as in the conventional gas sensors, and the gas absorbing liquid only has to be provided so as to be in contact with the carbon nanotube, the configuration can be simplified correspondingly.

Further, according to the second aspect of the present invention, the change of the state of the gate insulating layer of the gas absorbing liquid, which occurs by absorption of the gas is directly reflected in the source-drain current that flows in the carbon nanotube, and therefore, gas detection sensitivity can be enhanced more than in the conventional gas sensors. Further, since surface chemical modification does not have to be performed for the carbon nanotube itself as in the conventional gas sensors, and the gas absorbing liquid only has to be provided so as to be in contact with the carbon nanotube and the gate electrode, the configuration can be simplified correspondingly.

REFERENCE SIGNS LIST

Figure 1:
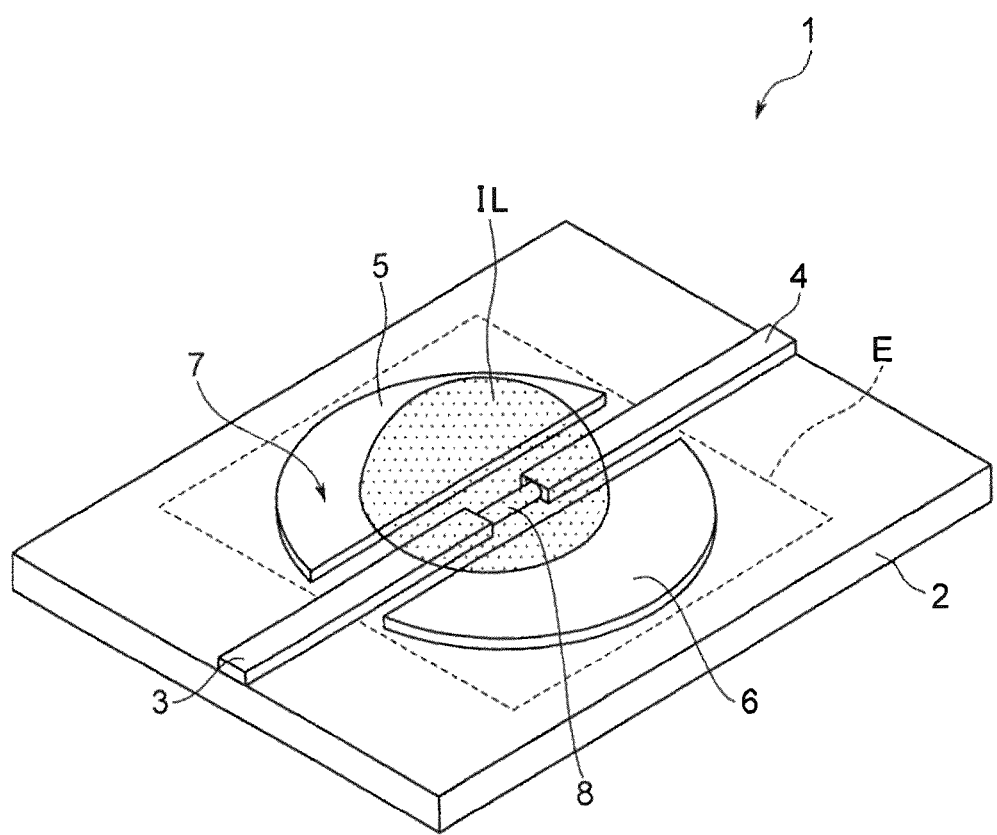
FIG. 1 is a perspective view showing a configuration of a gas sensor according to the present invention.

1, 31, 41, 51 Gas sensor
2 Substrate
3 Source electrode
4 Drain electrode
5 First gate electrode portion
6 Second gate electrode portion
7 Gate electrode
8 Carbon nanotube
IL Ionic liquid (gas adsorbing liquid)
42 Coating film (holding means)
52 Frame body (holding means)

DESCRIPTION OF EMBODIMENTS

Hereinafter, embodiments of the present invention will be described in detail based on the drawings.

(1) Outline of Gas Sensor of the Present Invention

In FIG. 1, a gas sensor according to the present invention is denoted by 1, and the gas sensor 1 is configured so as to be able to detect a gas, for example, such as $CO_2$ and $NH_3$, as a target of detection. In fact, the gas sensor 1 includes a source electrode 3 and a drain electrode 4 in band shapes on a substrate 2 formed into a plate shape, and a carbon nanotube 8 is provided between the source electrode 3 and the drain electrode 4. The source electrode 3 and the drain electrode 4 are formed from, for example, a Ti/Au material or a Cr/Au material, and disposed substantially rectilinearly with respective longitudinal directions being aligned with each other, so that a gap of approximately 1 µm is formed between an end portion of the source electrode 3 and an end portion of the drain electrode 4 that face each other.

The carbon nanotube 8 has one end side electrically connected to the end portion of the source electrode 3 and the other end side electrically connected to the end portion of the drain electrode 4, and is disposed so as to be positioned to form a straight line with the source electrode 3 and the drain electrode 4. Here, since the carbon nanotube 8 has a configuration in which a six-membered ring structure is rolled into a cylindrical shape in carbon, and has a large specific surface area, the carbon nanotube 8 correspondingly has a large contact surface to be in contact with an ionic liquid IL that will be described later, and also include excellent conductivity.

Figure 2:
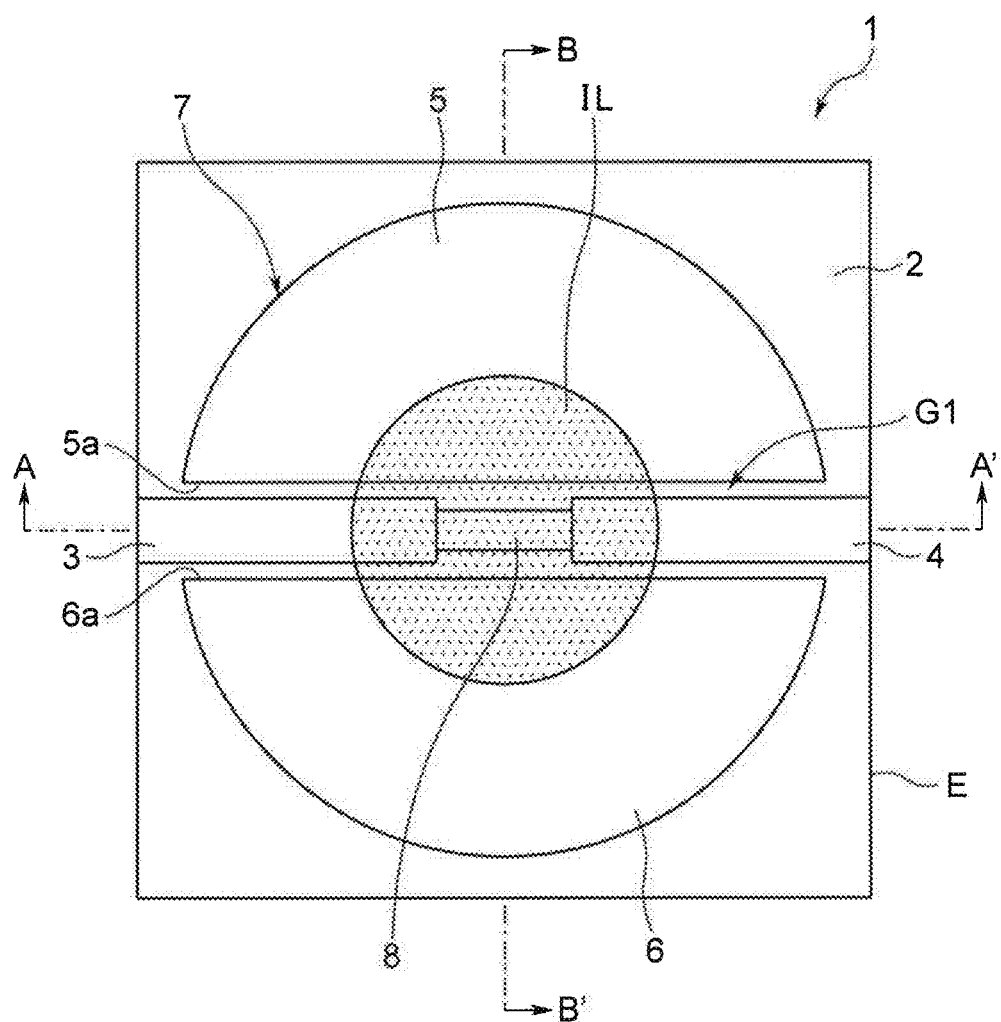
FIG. 2 is a schematic view showing a top surface configuration of the gas sensor according to the present invention.

The substrate 2 is provided with a gate electrode 7 formed from, for example, a Ti/Au material and a Cu/Au material, the ionic liquid IL is placed so as to be in contact with the gate electrode 7, and the carbon nanotube 8 is configured to be able to be contained in the ionic liquid IL. The gate electrode 7 is formed by a first gate electrode portion 5 and a second gate electrode portion 6 that are formed into the same shape and size, and the carbon nanotube 8, the source electrode 3 and the drain electrode 4 can be disposed in a gap G1 between the first gate electrode portion 5 and the second gate electrode portion 6. More specifically, in the case of this embodiment, as in FIG. 2 showing a top surface configuration of an area E of FIG. 1, the first gate electrode portion 5 and the second gate electrode portion 6 are formed into semi-circular shapes, a straight line portion 5a of the first gate electrode portion 5 and a straight line portion 6a of the second gate electrode portion 6 are disposed in parallel with each other with the predetermined gap G1 therebetween. In the gap G1 between these straight line portions 5a and 6a, the carbon nanotube 8, the source electrode 3 and the drain electrode 4 are disposed rectilinearly with respective longitudinal directions being aligned with one another.

The ionic liquid IL is placed in a semi-spherical shape over the first gate electrode portion 5, the second gate electrode portion 6, the source electrode 3 and the drain electrode 4 in such a manner as to cover the entire carbon nanotube 8, and is configured to be able to function as a gate insulating layer. The ionic liquid IL is configured so that a semi-spherical liquid surface is exposed to outside air, and can contain the carbon nanotube 8 that is located in a central portion of the first gate electrode portion 5, the second gate electrode portion 6, the source electrode 3 and the drain electrode 4. Here, the ionic liquid IL as a gas absorbing liquid is formed from, for example, [EMIM][$BF_4$](1-ethyl-3-methylimidazolium Tetrafluoroborate), [BMIM][$BF_4$](1-Butyl-3-methylimidazolium Tetrafluoroborate), [BMIM][$PF_6$](1-Butyl-3-methylimidazolium Hexafluorophosphate), or [OMIM][Br](1-n-octyl-3-methylimidazolium bromide), besides the above, [Hmpy][$Tf_2N$], [HMIM][$Tf_2N$], [BMIM][$Tf_2N$], [$C_6H_4F_9$min][$Tf_2N$], [AMIM][$BF_4$], [Pabim][$BF_4$], [Amim][DCA], [Am-im][BF$_4$], [BMIM][BF$_4$]+PVDF, [C$_3$NH$_2$mim][CF$_6$SO$_3$]+PTFE, [C$_3$NH$_2$mim][Tf$_2$N]+PTFE, [H$_2$NC$_3$H$_6$mim][Tf$_2$N]+cross-linked Nylon66, P[VBBI][BF$_4$], P[VBBI][BF$_4$], P[VBBI][Tf$_2$N], P[VBTMA][BF$_4$], P[MATMA][BF$_4$] or the like, and in accordance with the kind of a gas to be a target of detection, the ionic liquid that can absorb the gas can be properly selected.

Here, when the gas sensor 1 that can detect CO$_2$, for example, is provided, [EMIM][BF$_4$], [BMIM][BF$_4$], [BMIM][PF$_6$], [Hmpy][Tf$_2$N], [HMIM][Tf$_2$N], [BMIM][Tf$_2$N], [C$_6$H$_4$F$_9$mim][Tf$_2$N], [AMIM][BF$_4$], [Pabim][BF$_4$], [Am-im][DCA], [Am-im][BR$_4$], [BMIM][BF$_4$]+PVDF, [C$_3$NH$_2$mim][CF$_6$SO$_3$]+PTFE, [C$_3$NH$_2$mim][Tf$_2$N]+PTFE, [H$_2$NC$_3$H$_6$mim][Tf$_2$N]+cross-linked Nylon66, P[VBBI][BF$_4$], P[MABI][BF$_4$], P[VBBI][Tf$_2$N], P[VBTMA][BF$_4$], P[MATMA][BF$_4$] or the like that can absorb CO$_2$ is used as the ionic liquid IL. Further, when the gas sensor 1 that can detect NH$_3$ is provided, ionic liquids that absorb water in general, such as [EMIM][BF$_4$] capable of absorbing NH$_3$ are used as the ionic liquid IL.

Note that to the ionic liquid IL, for example, PEI (polyethyleneimine) may be added. In the ionic liquid IL with PEI added thereto, the amino group of PEI transfers electric charges to the carbon nanotube 8, and can reduce the resistance value of the carbon nanotube 8. In the ionic liquid IL with PEI added thereto, PEI reacts with CO$_2$ and H$_2$O when the ionic liquid IL absorbs a gas, and the amino group of PEI decreases. Accordingly, in the gas sensor 1 that uses the ionic liquid IL to which PEI is added like this, the amino group of PEI in the ionic liquid IL decreases when the ionic liquid IL absorbs outside air with a high CO$_2$ content, as a result of which, the resistance value of the carbon nanotube 8 can increase, and an electric state of the carbon nanotube 8 can change in accordance with the CO$_2$ content in the outside air.

Further, in the aforementioned embodiment, the case in which the ionic liquid IL is applied as the gas absorbing liquid is described, but the present invention is not limited to this. For example, various other gas absorbing liquids such as hydroxide aqueous solutions of an alkali metal and an alkaline earth metal may be applied. Note that when hydroxide aqueous solutions of an alkali metal and an alkaline earth metal are used as the gas absorbing liquid, the gas absorbing liquids can absorb CO$_2$, and therefore, the gas sensor the detection target of which is CO$_2$ can be realized.

Figure 3:
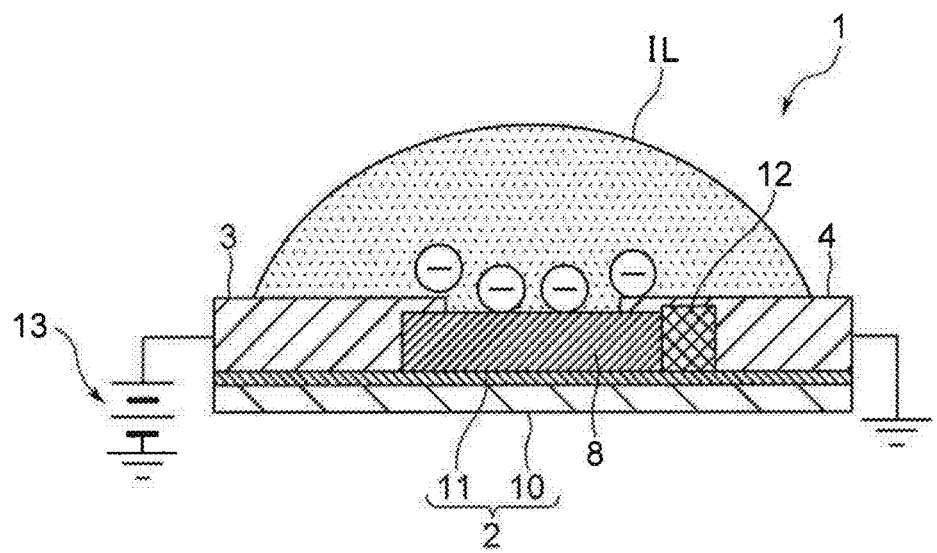
FIG. 3 is a sectional view showing a sectional configuration of an A-A' portion in FIG. 2.
Figure 4:
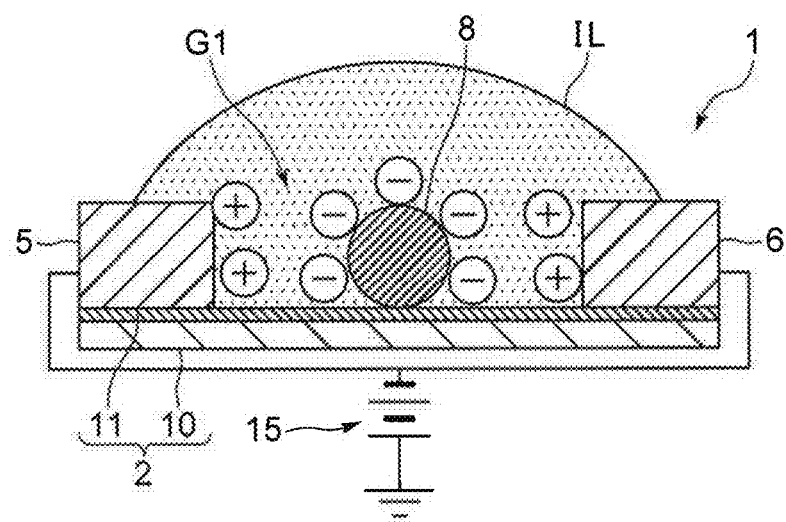
FIG. 4 is a sectional view showing a sectional configuration of a B-B' portion in FIG. 2.

Here, in the case of this embodiment, as in FIG. 3 showing a sectional configuration of an A-A' portion in FIG. 2, and FIG. 4 showing a sectional configuration of a B-B' portion in FIG. 2, the substrate 2 on which the ionic liquid IL is placed has a configuration in which a silicon oxide film 11 is formed on a silicon substrate 10, and has a configuration in which the source electrode 3, the drain electrode 4, the first gate electrode portion 5 and the second gate electrode portion 6 are provided on the silicon oxide film 11. Further, as shown in FIG. 3, the carbon nanotube 8 is configured so as to have one end side covered with the source electrode 3 and the other end side covered with the drain electrode 4, and to be capable of being electrically connected to the source electrode 3 and the drain electrode 4. Further, the carbon nanotube 8 can have both the ends reliably fixed to the substrate 2 by having both the ends covered with the source electrode 3 and the drain electrode 4, and therefore, can keep an electric connection state to the source electrode 3 and the drain electrode 4 as it is without being removed from the substrate 2 when the ionic liquid IL is dropped.

Further, the carbon nanotube 8 as above has a diameter of approximately 1 to 10 nm, and is formed by growing in a straight line shape along the silicon oxide film 11 from a catalyst portion 12 provided on the silicon oxide film 11. The catalyst portion 12 is formed from a material prepared by, for example, mixing Co and silica at a predetermined ratio, and is covered with the drain electrode 4 together with the other end of the carbon nanotube 8. The gas sensor 1 like this is configured so that a source-drain current is supplied to the drain electrode 4 from the source electrode 3 by a power supply 13 as shown in FIG. 3, and as shown in FIG. 4, a gate voltage can be applied to the first gate electrode portion 5 and the second gate electrode portion 6 by a power supply 15.

Thereby, as shown in FIG. 3 and FIG. 4, when the gate voltage is applied to the first gate electrode portion 5 that faces the carbon nanotube 8 in the gas sensor 1, a potential difference occurs in the ionic liquid IL, and electric charges are supplied to the carbon nanotube 8 to keep the balance. More specifically, when a negative voltage is applied to the first gate electrode portion 5, the electric charges in the ionic liquid IL are polarized as shown in FIG. 4, and negative electric charges gather on the surface of the carbon nanotube 8 as in FIG. 3 and FIG. 4. Further, in contrast with this, a positive voltage also can be applied to the first gate electrode portion 5, and in that case, the electric charges in the ionic liquid IL are similarly polarized, but positive electric charges gather on the surface of the carbon nanotube 8.

Figure 5:
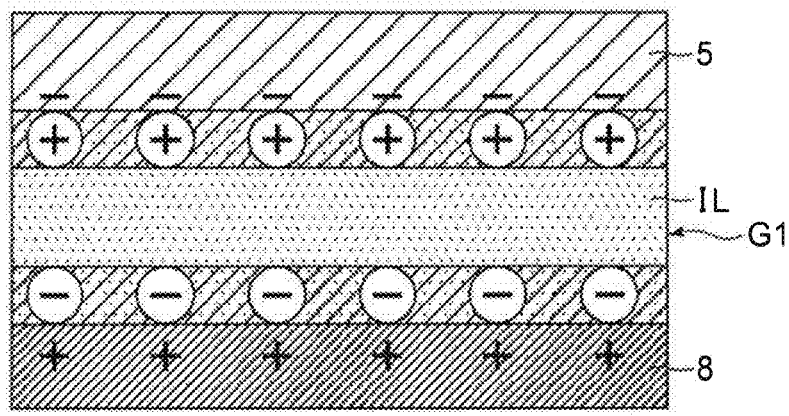
FIG. 5 is a schematic view presented for explanation of an electric double layer.

Thus, for example, when a negative voltage is applied to the gate electrode 7, in the gas sensor 1, anions in the ionic liquid IL gather on the side peripheral surface of the carbon nanotube 8, whereas cations in the ionic liquid IL gather on the first gate electrode portion 5 (the same applies to the second gate electrode portion 6), an electric double layer (two layers that are a layer in which marks of circled "−" are written and a layer in which marks of circled "+" are written in FIG. 5) is formed in the ionic liquid IL as shown in FIG. 5, and the ionic liquid IL can be a gate insulating layer.

Namely, in the gas sensor 1, a gate voltage $V_g$ is applied to the first gate electrode portion 5 and the second gate electrode portion 6, and a source-drain voltage $V_{sd}$ is applied between the source electrode 3 and the drain electrode 4, whereby an extremely thin gate insulating layer is formed in the ionic liquid IL, a source-drain current $I_{sd}$ flows in the carbon nanotube 8, and the gas sensor can operate as a transistor. Further, in addition to this, in the gas sensor 1 formed with the configuration like this, when the ionic liquid IL absorbs a gas that is a target of detection, the state of the gate insulating layer in the ionic liquid IL can be changed in accordance with the absorption amount of the gas, and source-drain current/gate voltage characteristics also can change in accordance with the change of the state of the gate insulating layer.

With the gas sensor 1, such the change of the source-drain current/gate voltage characteristics is measured, and the gas that is a target of detection can be detected based on the change of the source-drain current/gate voltage characteristics. Further, with the gas sensor 1, the change amount of the source-drain current/gate voltage characteristics is measured, and when the change amount is large, it is indicated that a gas concentration in the gas (hereinafter, also simply called outside air) around the ionic liquid IL is high, whereas when the change amount is small, it is indicated that the gas concentration in the outside air is low, so that the gas concentration in the outside air can be estimated.

Figure 6:
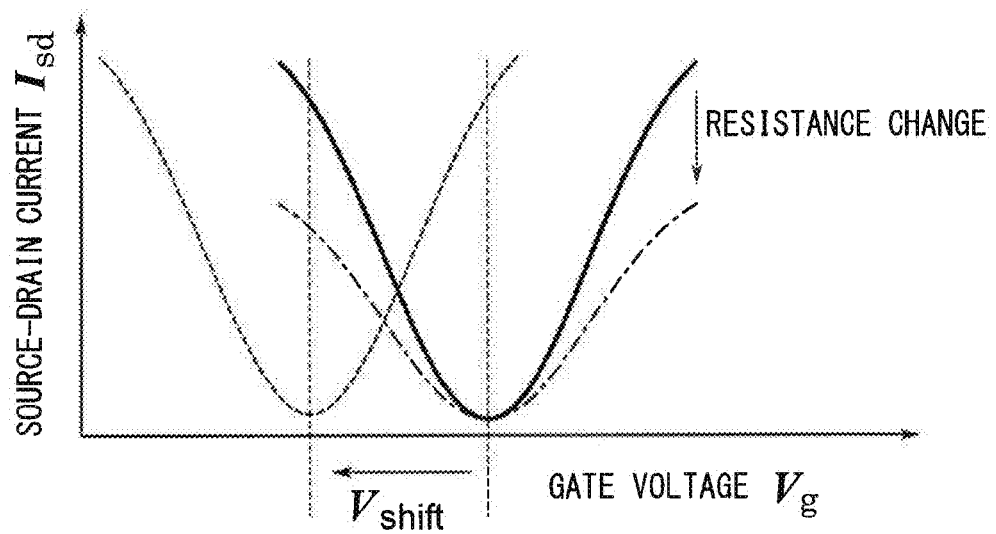
FIG. 6 is a graph showing change of a source-drain current and a gate voltage.

In practice, in the case of the gas sensor 1 having a metallic carbon nanotube, a waveform close to a substantially V-shape can be obtained as the relationship between the source drain current $I_{sd}$ and the gate voltage $V_g$ when the gas that is a target of detection is not contained in the gas around the ionic liquid IL, as shown in FIG. 6. In contrast with this, when the gas around the ionic liquid IL has a high concentration of the gas that is a target of detection, the gate voltage $V_g$ in the gas sensor 1 can shift by a shift voltage $V_{shift}$. When the gas concentration in outside air becomes high, the shift voltage $V_{shift}$ can increase in proportion thereto. As above, in the gas sensor 1 of the present invention, detection of the gas contained in outside air and estimation of the content of the gas are enabled based on a change of the source-drain current $I_{sd}$, and the change of the gate voltage $V_g$ that occurs due to the change of the source-drain current $I_{sd}$.

Note that in the aforementioned embodiment, the gas sensor 1 is described, which is provided with the gate electrode 7, applies the gate voltage $V_g$ to the first gate electrode portion 5 and the second gate electrode portion 6 that configure the gate electrode 7, forms the electric double layer on the surface of the carbon nanotube 8 in the ionic liquid IL, and measures the change of the source-drain current $I_{sd}$ which flows in the carbon nanotube 8 as a result of the state of the electric double layer changing by the ionic liquid IL absorbing a gas. The present invention is not limited to this, and may be a gas sensor that is not provided with the gate electrode 7, and simply measures the change of the source-drain current $I_{sd}$ that flows in the carbon nanotube 8 between the source electrode 3 and the drain electrode 4 by the ionic liquid IL absorbing a gas.

Namely, in the gas sensor 1, negative electric charges in the ionic liquid IL gather on the surfaces of the carbon nanotube 8 even when the gate voltage $V_g$ is 0[V], because the carbon nanotube 8 having a large number of holes is in the ionic liquid IL. Therefore, in the gas sensor 1, the states of the negative electric charges and positive electric charges in the ionic liquid IL change as a result of the ionic liquid IL absorbing a gas, and in response to this, the source-drain current $I_{sd}$ that flows in the carbon nanotube 8 can also change. Thus, with the gas sensor 1, detection of the gas contained in outside air and estimation of the content of the gas are enabled from the change of the source-drain current $I_{sd}$ that flows in the carbon nanotube 8, even though the gate electrode 7 is not provided.

(2) Method for Producing Gas Sensor

Figure 7:
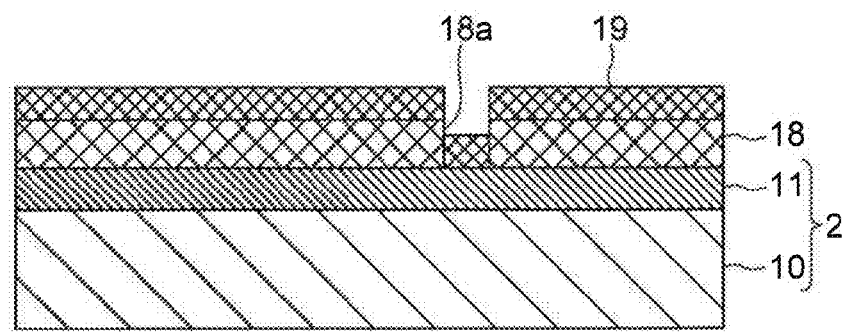
FIG. 7 is a schematic view presented for explanation (1) of a method of producing the gas sensor.

Next, a method of producing the gas sensor 1 of the present invention will be described. In the case of this embodiment, a substrate 2 in which a silicon oxide film 11 is formed on a silicon substrate 10 is prepared first of all, and a resist layer of a predetermined pattern is formed on the silicon oxide film 11. Next, as shown in FIG. 7, a catalyst layer 19 is formed on the resist layer 18 on the substrate 2 by spin coating, and the catalyst layer 19 is also formed on the silicon oxide film 11 that is exposed in an opening 18a formed in the resist layer 18. Note that for the catalyst layer 19, a catalyst material formed by mixing, for example, Co and fumed silica at a ratio of 1:10, or the like is used. Next, the resist layer 18 is removed by lift-off, only the catalyst layer 19 that is formed in the opening 18a is left, and the catalyst portion 12 of 3 to 7 [μm] is formed in rectangular shape.

Figure 8:
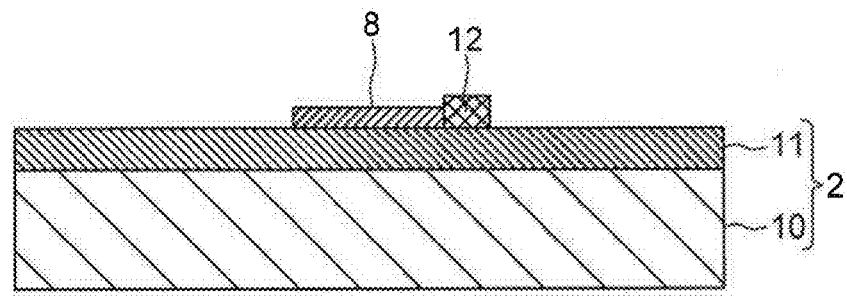
FIG. 8 is a schematic view presented for explanation (2) of the method of producing the gas sensor.
Figure 9:
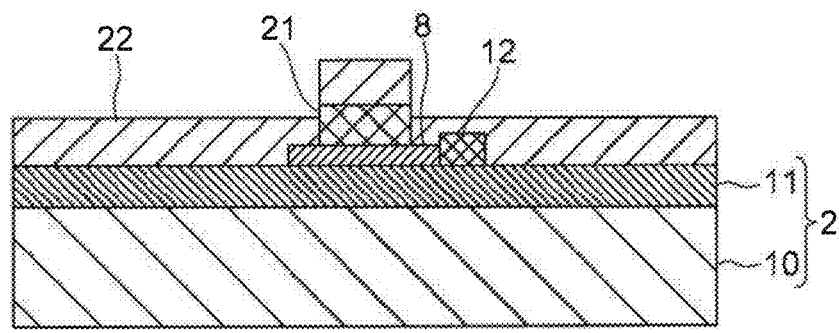
FIG. 9 is a schematic view presented for explanation (3) of the method of producing the gas sensor.
Figure 10:
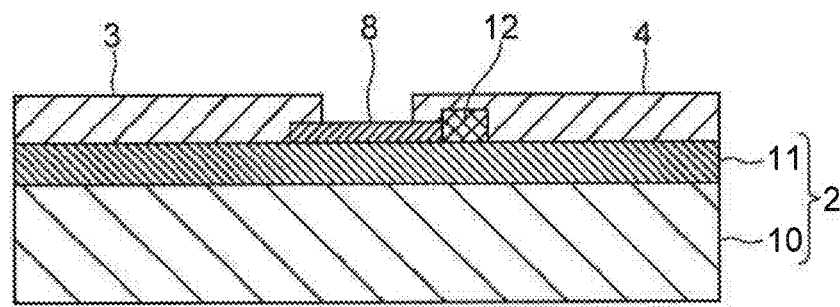
FIG. 10 is a schematic view presented for explanation (4) of the method of producing the gas sensor.

Next, a carbon is grown from the catalyst portion 12 by a chemical vapor deposition method (CVD), and the carbon nanotube 8 that extends rectilinearly from the catalyst portion 12 is formed on the silicon oxide film 11 as shown in FIG. 8. And then, after the entire surface is coated with a resist layer, the resist layer is patterned by exposure, and as shown in FIG. 9, after a resist layer 21 is left in central regions of the carbon nanotube 8 that are exposed in the ionic liquid IL, for example, an electrode layer 22 formed from Ti/Au (5/50) is formed on the entire surface. Next, the resist layer 21 is removed by lift-off and the electrode layer 22 is patterned, whereby the central regions of the carbon nanotube 8 is exposed, and the source electrode 3, the drain electrode 4, and further the first gate electrode portion 5 and the second gate electrode portion 6 which are not illustrated are formed on the silicon oxide film 11 as shown in FIG. 10.

Figure 11:
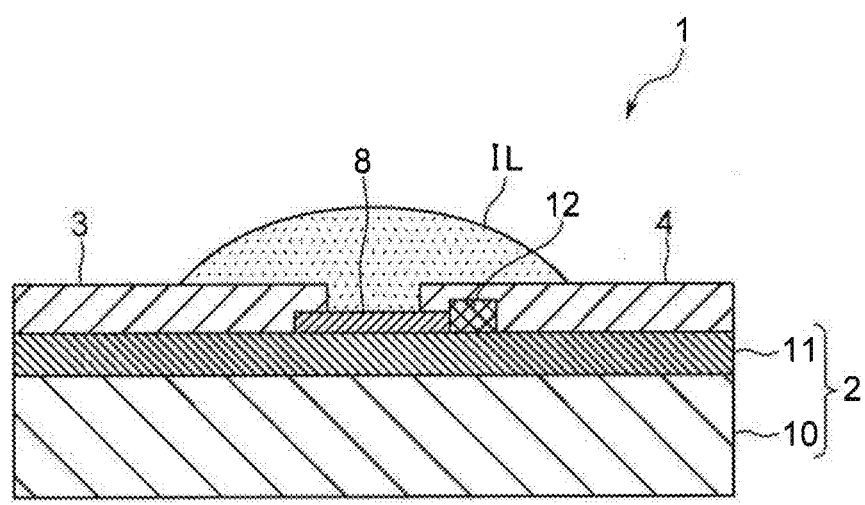
FIG. 11 is a schematic view presented for explanation (5) of the method of producing the gas sensor.
Figure 12:
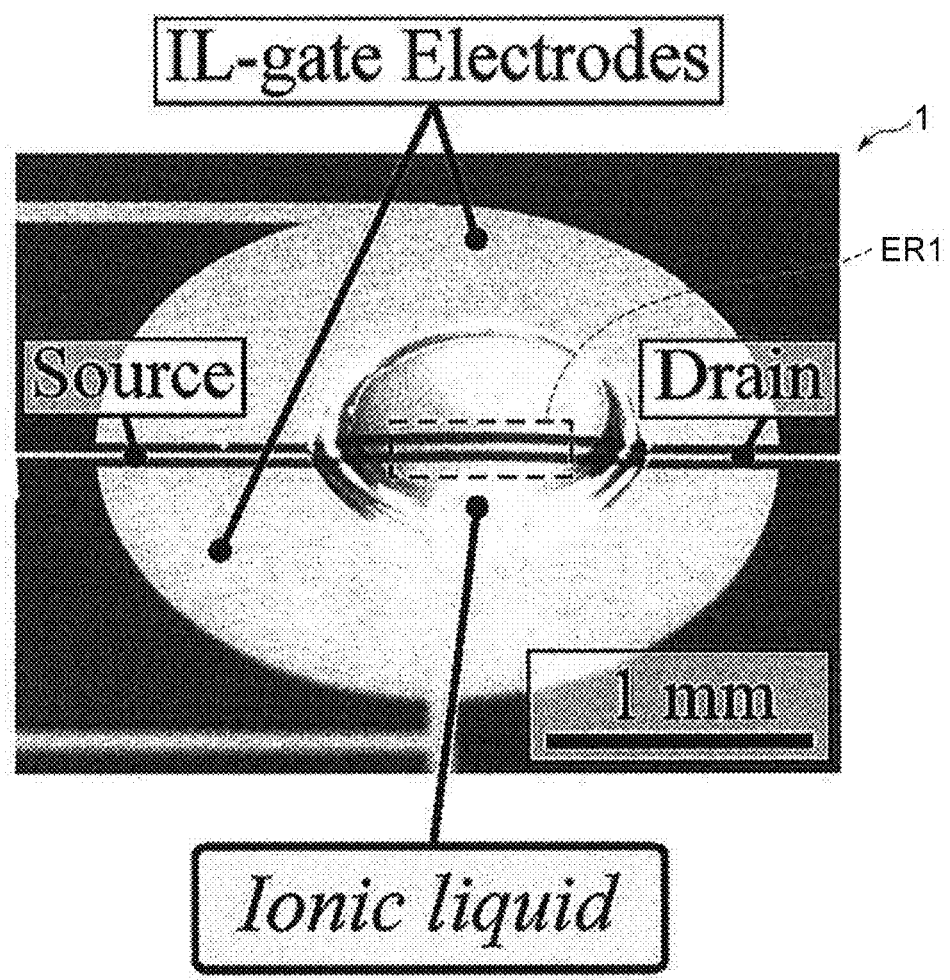
FIG. 12 is a photograph showing a configuration of the gas sensor actually produced.
Figure 13:
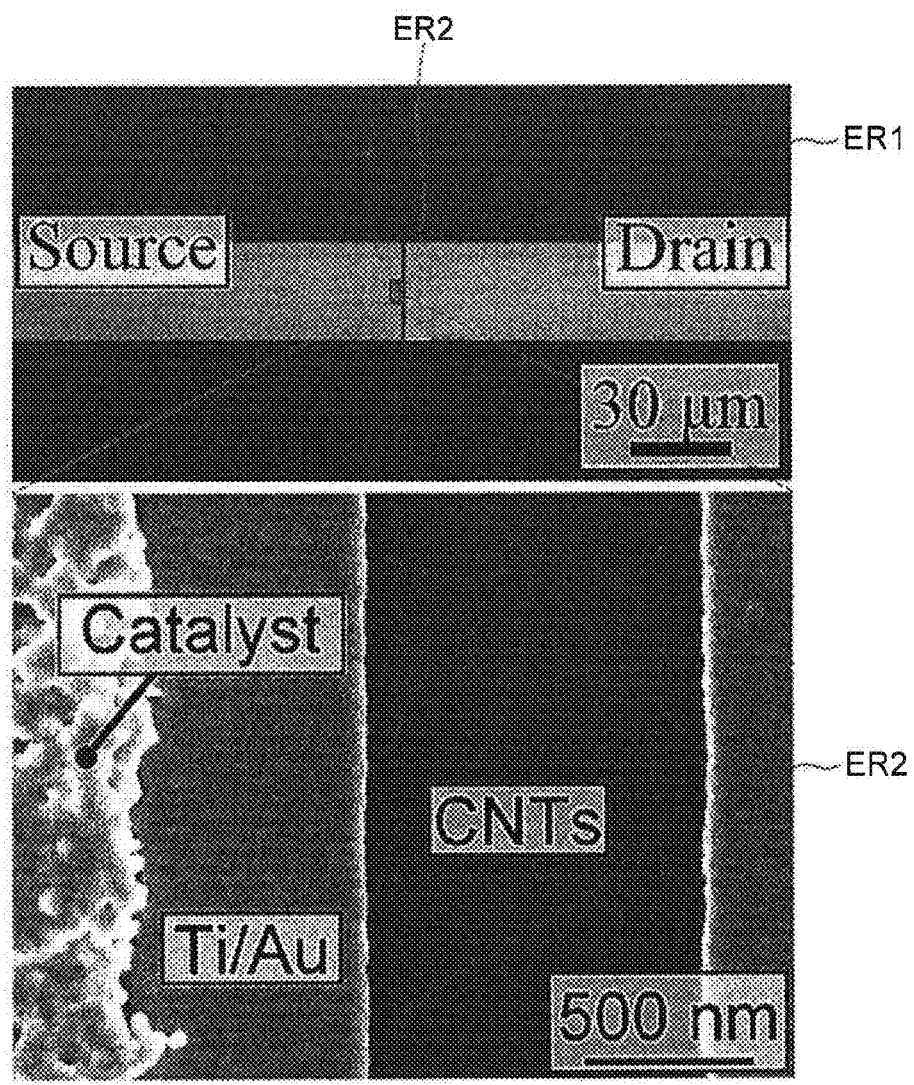
FIG. 13 is a photograph of a part of FIG. 12 that is enlarged, and an SEM photograph showing a detailed configuration of a carbon nanotube.

Next, as shown in FIG. 11, the ionic liquid IL is dropped onto the substrate 2 in such a manner as to cover the entire carbon nanotube 8 that are exposed between the source electrode 3 and the drain electrode 4, whereby as shown in FIG. 12, the gas sensor 1 can be produced, in which the ionic liquid IL (described as "Ionic Liquid" in the drawing) is in contact with the source electrode 3 (described as "Source" in the drawing), the drain electrode 4 (described as "Drain" in the drawing) and the gate electrode 7 (the first gate electrode portion 5 and the second gate electrode portion 6, described as "IL-gate Electrodes" in the drawing). As shown in FIG. 13 in which an area ER1 in FIG. 12 is enlarged, and a SEM photograph in which an area ER2 of FIG. 13 is further enlarged, in the gas sensor 1 which is produced in this manner, the carbon nanotube 8 contained in the ionic liquid IL is formed in a very small gap between the source electrode 3 and the drain electrode 4, and has an extremely microscopic structure. Note that the wording "Catalyst" in FIG. 13 indicates the catalyst portion 12 that is buried in the drain electrode 4, and the shape of the catalyst portion 12 can be confirmed from the drain electrode 4 that is located on an outer side of the catalyst portion 12.

(3) Verification Test

Next, various verification tests will be described. Here, in accordance with the production method described above, the source electrode 3, the drain electrode 4, and the gate electrode 7 were respectively formed from Ti/Au (film thickness 5 [nm]/50 [nm]), the carbon nanotube 8 was formed from the catalyst portion 12 formed by mixing Co and fumed silica at 1:10, and the gas sensor 1 in which the gap between the source electrode 3 and the drain electrode 4 was set at 1 [μm] and the resistance value of the carbon nanotube 8 was set at 5 to 100 [kΩ] was produced. Subsequently, the relationship between the source-drain current $I_{sd}$ flowing to the drain electrode 4 through the carbon nanotube 8 from the source electrode 3 and the gate voltage $V_g$ that was applied to the gate electrode 7 when a gas that was a target of detection was not contained in outside air was examined in the gas sensor 1, the result as shown in FIG. 14 was obtained.

Figure 14:
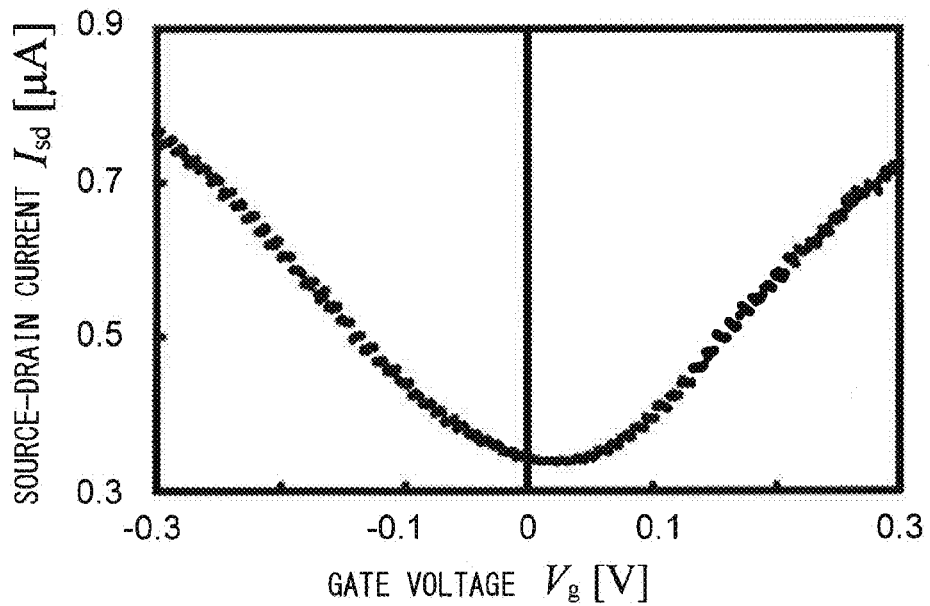
FIG. 14 is a graph showing a relation of a source-drain current $I_{sd}$ and a gate voltage $V_g$, obtained by the gas sensor.

Note that FIG. 14 shows the relation of the source-drain current $I_{sd}$ and the gate voltage $V_g$ when the source-drain voltage $V_{sd}$ between the source electrode 3 and the drain electrode 4 of the gas sensor 1 was set at 10 [mV], and the gate voltage $V_g$ that was applied to the gate electrode 7 was increased from −0.3 [V] to 0.3 [V] at 5 [mV/sec]. From FIG. 14, it was confirmed that in the gas sensor 1, a waveform close to a gentle V-shape is obtained when the gas that is a target of detection is not contained in outside air.

Figure 15:
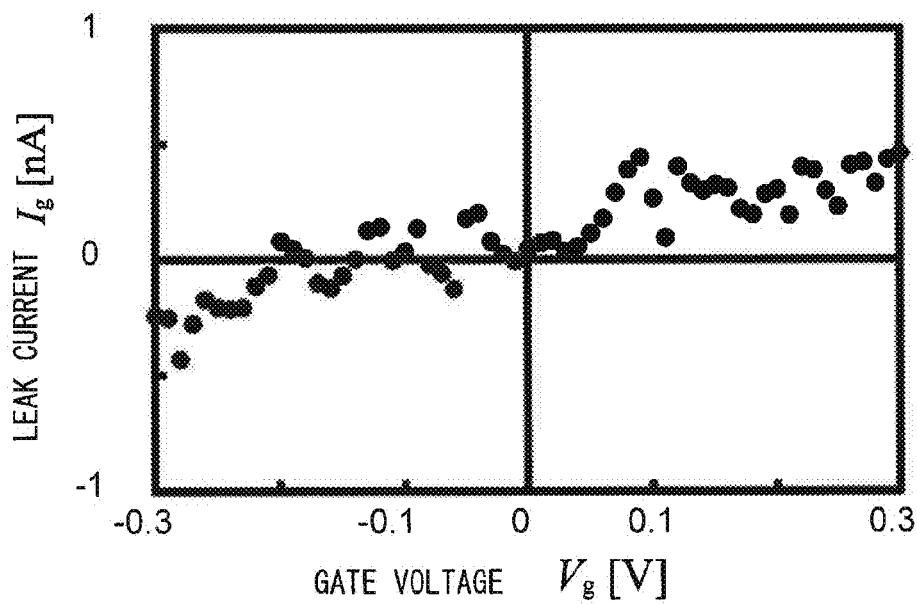
FIG. 15 is a graph showing a relation of a leak current $I_g$ and the gate voltage $V_g$.

Further, when the leak current $I_g$ that flows in the gate electrode 7 when the source drain voltage $V_{sd}$ was set at 0 [mV] was examined in the gas sensor 1, the result as shown in FIG. 15 was obtained. When the result shown in FIG. 15 and the source-drain current $I_{sd}$ were compared, it was found out that the leak current $I_g$ becomes approximately 0.01[%] with respect to the source-drain current $I_{sd}$ between the gate voltages $V_g$ of −0.3 [V] to 0.3 [V], and it was confirmed that the leak current $I_g$ is a very small ignorable value.

Figure 16:
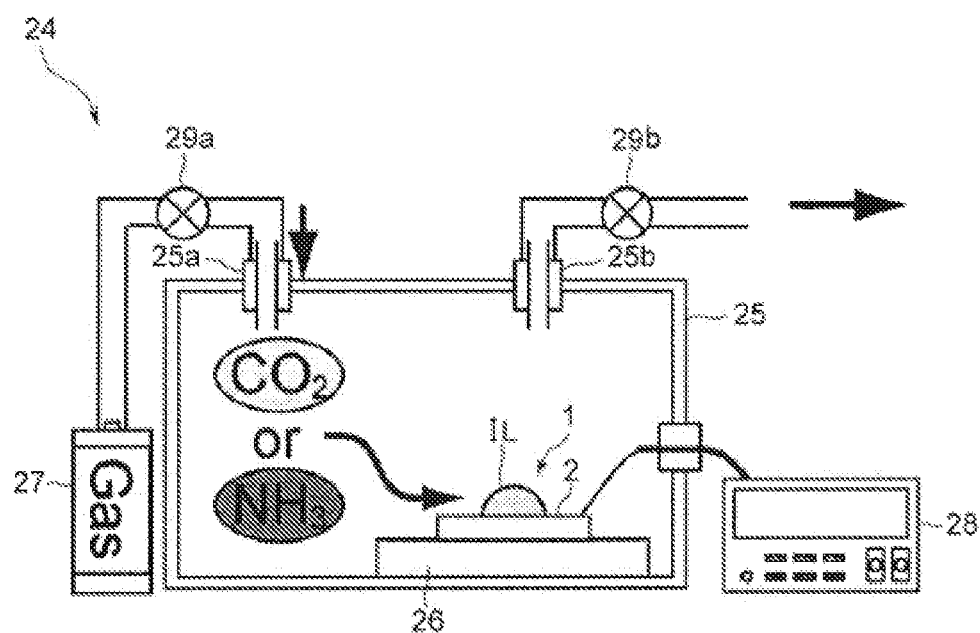
FIG. 16 is a schematic view showing an entire configuration of an experimental apparatus.

Next, with use of an experimental apparatus 24 as shown in FIG. 16, a verification test was performed concerning whether or not the gas that is a target of detection is detectable in the gas sensor 1. In practice, in the experimental apparatus 24, the gas that is a target of detection was supplied into a chamber 25 of 300×300×100 [mm$^3$] through a supply port 25a from a gas storage section 27 via a valve 29a, and the gas was discharged to an outside of the chamber 25 from a discharge port 25b via a valve 29b. Further, in the experimental apparatus 24, the gas sensor 1 was placed on a base 26 in the chamber 25, and a measuring device 28 provided outside the chamber 25 and the gas sensor 1 in the chamber 25 were connected while a sealed state of the chamber 25 is kept.

In the experimental apparatus 24 as above, the gas sensor 1 using [EMIM][BF$_4$] as the ionic liquid IL was installed in the chamber 25 first of all, after which, the inside of the chamber 25 was filled with air (Air) that does not contain the gas that is a target to be detected, and the relation between the source-drain current $I_{sd}$ and the gate voltage $V_g$ in the gas sensor 1 at this time was examined. Thereafter, $CO_2$ was supplied into the chamber 25, the inside of the chamber 25 was filled with a mixture gas prepared by mixing 12[%] of $CO_2$ into outside air (Air), and the relation of the source-drain current $I_{sd}$ and the gate voltage $V_g$ in the gas sensor 1 was also examined after stabilization.

Figure 17:
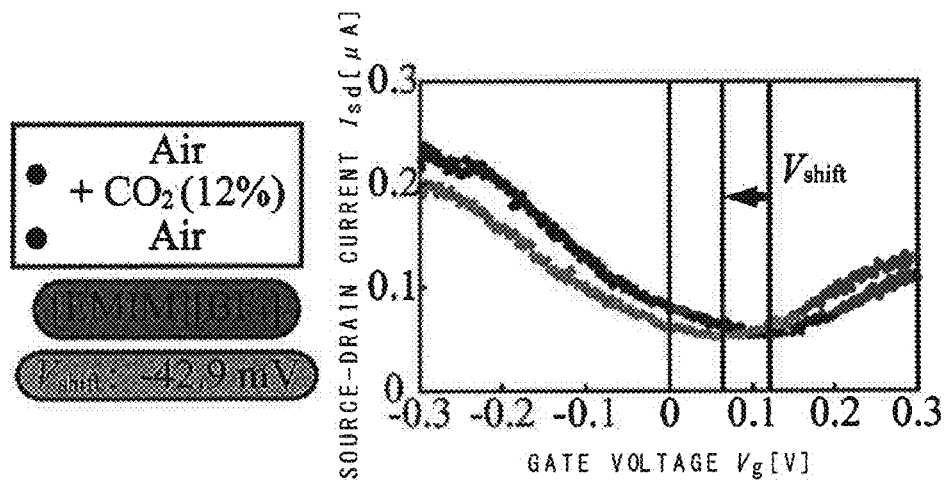
FIG. 17 is a graph showing relation of the source-drain current $I_{sd}$ and the gate voltage $V_g$ in the case of a mixture gas of $CO_2$ and outside air, and in the case of only outside air.

More specifically, when the source-drain voltage $V_{sd}$ was set at 10 [mV] in the gas sensor 1, and the source-drain current $I_{sd}$ was measured as the gate voltage $V_g$ to be applied to the gate electrode 7 was increased from −0.3 [V] to 0.3 [V] at 5 [mV/sec], the result as shown in FIG. 17 was obtained. From FIG. 17, it was confirmed that when $CO_2$ that is a target of detection is mixed in outside air, the gate voltage $V_g$ shifts by −42.9 [mV] as compared with the case of ordinary outside air. Accordingly, it was confirmed that in the gas sensor 1, the ionic liquid IL absorbs $CO_2$ as a target of detection, as a result of which, the state of the gate insulating layer that is formed in the ionic liquid IL changes, the source-drain current $I_{sd}$ changes, and the shift voltage $V_{shift}$ if is generated. Thus, it was confirmed that the gas sensor 1 of the present invention can detect $CO_2$ in the outside air around the ionic liquid IL, by measuring the change of the source-drain current $I_{sd}$.

Figure 18:
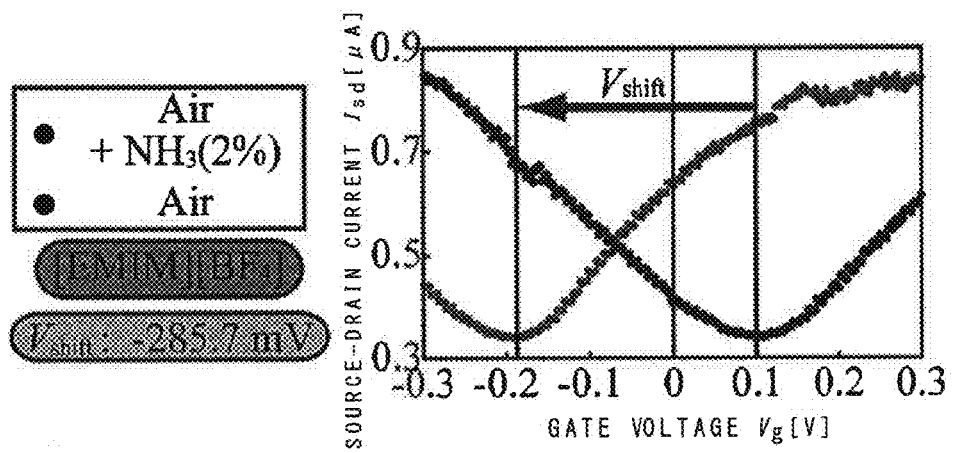
FIG. 18 is a graph showing relation of the source-drain current $I_{sd}$ and the gate voltage $V_g$ in the case of a mixture gas of $NH_3$ and outside air, and in the case of only outside air.

Next, when the gas that is a target of detection was changed from $CO_2$ to $NH_3$ after the inside of the chamber 25 was refreshed, and a new experiment was performed under the same experimental conditions as described above, the result as shown in FIG. 18 was obtained. In this experiment, $NH_3$ was supplied into the chamber 25, the inside of the chamber 25 was filled with a mixture gas prepared by mixing 2[%] of $NH_3$ into outside air (Air), and after stabilization, the relation between the source-drain current $I_{sd}$ and the gate voltage in the gas sensor 1 was examined. From FIG. 18, it was confirmed that when $NH_3$ that is a target of detection is mixed in the outside air in the gas sensor 1 of the present invention, the gate voltage $V_g$ shifts by −285.7 [mV] as compared with the case of air (Air) that does not contain a gas. Accordingly, it was confirmed that in the gas sensor 1, the ionic liquid IL absorbs $NH_3$ as the target of detection, as a result of which, the state of the gate insulating layer which is formed in the ionic liquid IL changes, the source-drain current $I_{sd}$ changes, and the shift voltage $V_{shift}$ is generated. Thus, it was confirmed that the gas sensor 1 of the present invention can detect $NH_3$ in the outside air around the ionic liquid IL by measuring the change of the source-drain current $I_{sd}$.

Figure 19:
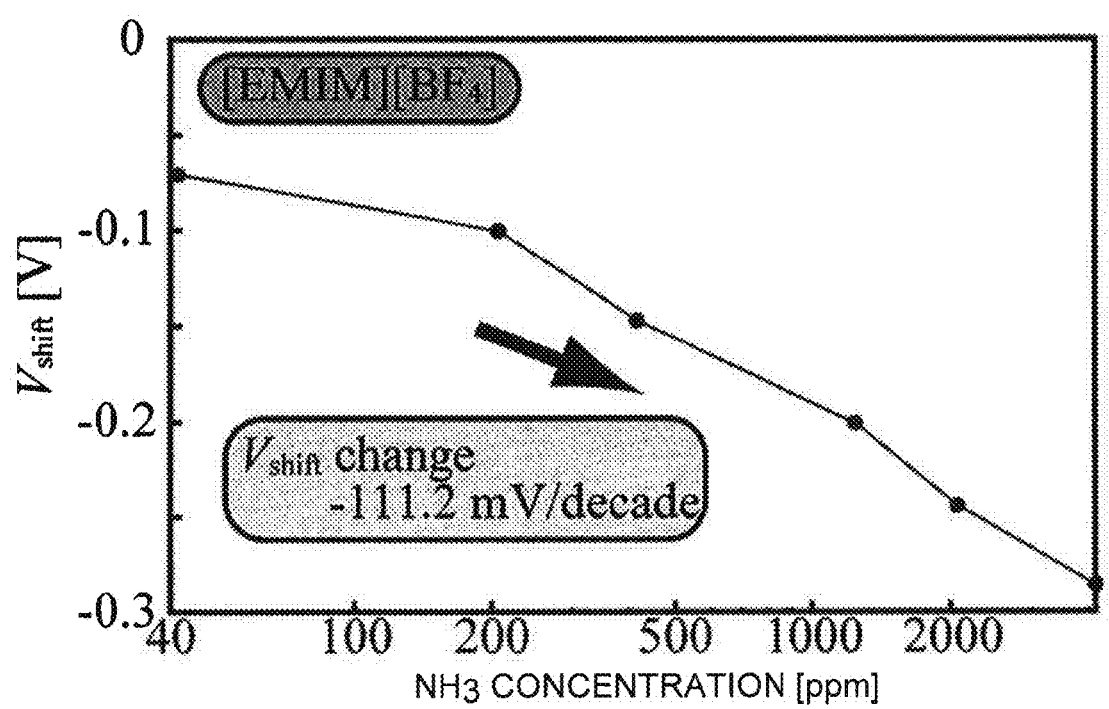
FIG. 19 is a graph showing a relation of a shift voltage $V_{shift}$ and an $NH_3$ concentration.

Next, when the inside of the chamber 25 was refreshed, and thereafter, the shift voltage $V_{shift}$ was measured as the concentration of $NH_3$ was changed from 40 to 4000 [ppm], the result as shown in FIG. 19 was obtained. From FIG. 19, it was confirmed that in the gas sensor 1, the shift voltage $V_{shift}$ changes linearly with respect to concentration logs of $NH_3$, and from this, it was also confirmed that based on the change of the shift voltage $V_{shift}$ that occurs as a result of the source-drain current $I_{sd}$ changing, the $NH_3$ concentration can be estimated.

Further, apart from the above, the gas sensor 1 using ionic liquid IL prepared by mixing PEI (branched, M. W. 10,000) into [EMIM][BF$_4$] as the ionic liquid IL, and using a metallic carbon nanotube as the carbon nanotube 8 was prepared. Incidentally, concerning whether the carbon nanotube 8 is a metallic carbon nanotube or a semiconductor carbon nanotube that will be described later, an I-V characteristic was measured after the carbon nanotube 8 was produced, and determination was performed from the shape of the curve of the I-V characteristic.

Subsequently, after the gas sensor 1 having the configuration like this was installed in the chamber 25, the inside of the chamber 25 was filled with air (Air), and the relation of the source-drain current $I_{sd}$ and the gate voltage $V_g$ in the gas sensor 1 at this time was examined. Thereafter, $CO_2$ was supplied into the chamber 25, the inside of the chamber 25 was filled with a mixture gas prepared by mixing $CO_2$ into the air (Air) by 24[%], and after stabilization, the relation of the source-drain current $I_{sd}$ and the gate voltage $V_g$ in the gas sensor 1 was also examined. In this experiment, when the source-drain voltage $V_{sd}$ of the gas sensor 1 was set at 10 [mV], and the source-drain current $I_{sd}$ was measured at the gate voltages $V_g$ of −0.3 [V] to 0.3 [V] as in the aforementioned experiment, the result as shown in FIG. 20 was obtained.

Figure 20:
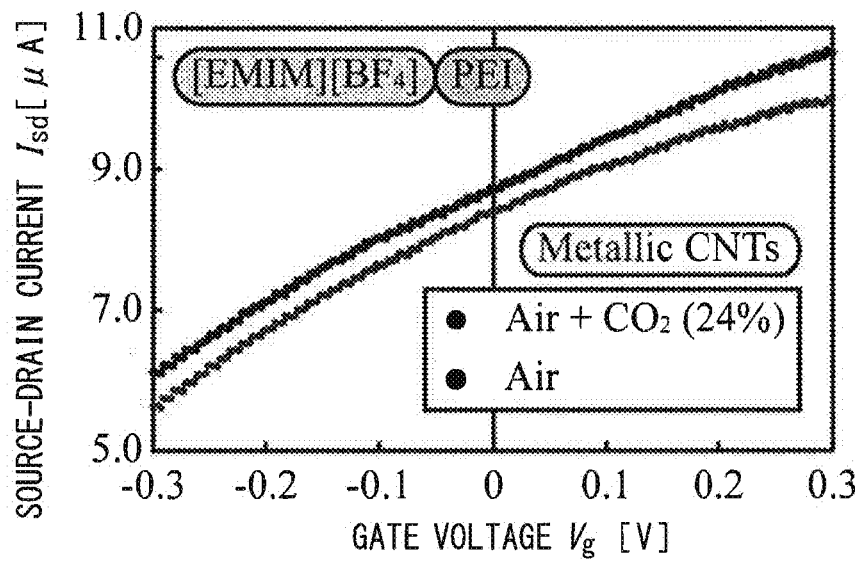
FIG. 20 is a graph showing relation of the source-drain current $I_{sd}$ and the gate voltage $V_g$ by the gas sensor using a metallic carbon nanotube.

From FIG. 20, it was confirmed that in the gas sensor 1 as above, the gate voltage $V_g$ shifts when $CO_2$ that is the target of detection is mixed in the outside air, as compared with the case of the air (Air) that does not contain $CO_2$. Accordingly, it was also confirmed that in this gas sensor 1, the ionic liquid IL absorbs $CO_2$ as the target of detection, as a result of which, the state of the gate insulating layer formed in the ionic liquid IL changes, the source-drain current $I_{sd}$ that flows in the metallic carbon nanotube changes, and the shift voltage $V_{shift}$ is generated, and thus, it was confirmed that by measuring the change of the source-drain current $I_{sd}$, $CO_2$ in the outside air can be detected.

Further, apart from the above, the gas sensor 1 using the ionic liquid IL prepared by mixing PEI (branched, M. W. 10,000) into [EMIM][BF$_4$] that is the same as described above as the ionic liquid IL, and using a semiconductor carbon nanotube as the carbon nanotube 8 was prepared.

Subsequently, after the gas sensor 1 having the configuration as above was installed in the chamber 25, the inside of the chamber 25 was filled with air (Air), and the relation of the source-drain current $I_{sd}$ and the gate voltage $V_g$ in the gas sensor 1 at this time was examined. Thereafter, $CO_2$ was supplied into the chamber 25, the inside of the chamber 25 was filled with a mixture gas in which $CO_2$ was mixed into the air (Air) by 25[%], and after stabilization, the relation between the source-drain current $I_{sd}$ and the gate voltage $V_g$ in the gas sensor 1 was also examined. In this experiment likewise, when the source-drain voltage $V_{sd}$ of the gas sensor 1 was set at 10 [mV], and the source drain current $I_{sd}$ was measured at the gate voltages $V_g$ of −0.3 [V] to 0.3 [V], as in the above experiment, the result as shown in FIG. 21 was obtained.

Figure 21:
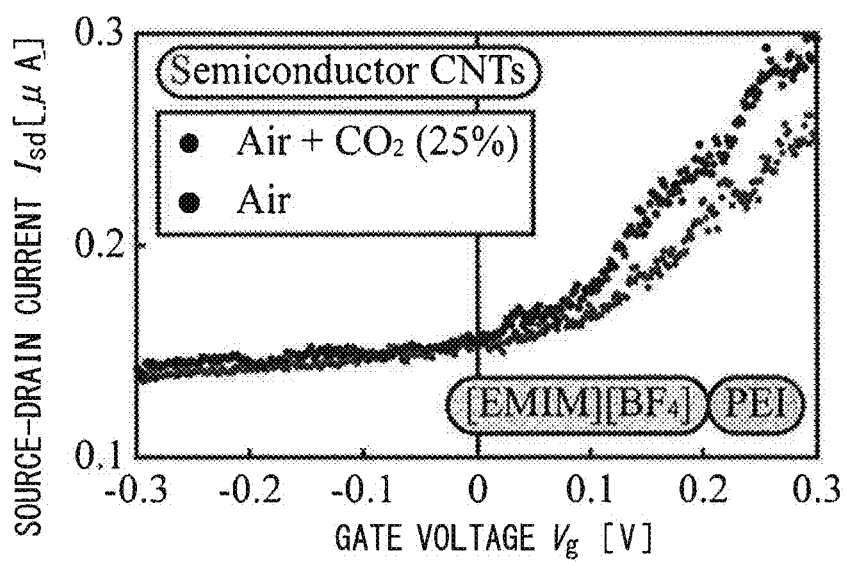
FIG. 21 is a graph showing relation of the source-drain current $I_{sd}$ and the gate voltage $V_g$ by the gas sensor using a semiconductor carbon nanotube.

From FIG. 21, it has been confirmed that in the gas sensor 1 as above, the gate voltage $V_g$ shifts when $CO_2$ that is the target of detection is mixed in the outside air, as compared with the case of the air (Air) that does not contain $CO_2$. Accordingly, it was confirmed that in this gas sensor 1, the ionic liquid IL absorbs $CO_2$ as the target of detection, as a result of which, the electric state of the gate insulating layer formed in the ionic liquid IL changes, the source-drain current $I_{sd}$ that flows in the semiconductor carbon nanotube changes, and the shift voltage $V_{shift}$ is generated. And thus, it was confirmed that by measuring the change of the source-drain current $I_{sd}$, $CO_2$ in the outside air can be detected.

(4) Operation and Effect

In the above configuration, the gas sensor 1 is configured such that the carbon nanotube 8 is provided between the source electrode 3 and the drain electrode 4 on the substrate 2, and the carbon nanotube 8 is covered with the ionic liquid IL. In the gas sensor 1 like this, the carbon nanotube 8 having a large number of holes is located in the ionic liquid IL, and thereby the negative electric charges in the ionic liquid IL gather on the surface of the carbon nanotube 8. Thereby, when the ionic liquid IL absorbs a gas that is a target of detection in the gas sensor 1, the state of the negative electric charges that gather on the surface of the carbon nanotube 8 in the ionic liquid IL changes, and with this change, the source-drain current $I_{sd}$ that flows in the carbon nanotube 8 also changes, whereby based on the tendency of the change of the source-drain current $I_{sd}$, the gas in the outside air can be detected.

Further, in the gas sensor 1, the carbon nanotube 8 is provided between the source electrode 3 and the drain electrode 4 on the substrate 2, the ionic liquid IL to be the gate insulating layer is provided in contact with the carbon nanotube 8 and the gate electrode 7 on the substrate 2, and a gate voltage is applied to the ionic liquid IL via the gate electrode 7. Thereby, in the gas sensor 1, the electric double layer having the gate insulating layer is formed in the ionic liquid IL that absorbs a gas, and the gas sensor 1 can operate as a transistor capable of measuring the source-drain current $I_{sd}$ that flows in the carbon nanotube 8.

In the gas sensor 1 like this, the state of the gate insulating layer in the ionic liquid IL changes when the ionic liquid IL absorbs the gas that is a target of detection, and the source-drain current $I_{sd}$ that flows in the carbon nanotube in the ionic liquid IL changes in response to the state of the gate insulating layer. Therefore, the change of the source-drain current $I_{sd}$ is measured, and the gas in the outside air can be detected based on the tendency of the change of the source-drain current $I_{sd}$.

Here, in the conventional back gate type gas sensor (not illustrated) shown in National Publication of International Patent Application No. 2007-505323, a silicon oxide film with a film thickness of 150 to 200 [nm], for example, is used as a gate insulating layer between the silicon back gate and the carbon nanotube, and therefore, in order to operate the gas sensor as a transistor, a gate voltage of approximately 15 [V] at the maximum is needed. In contrast with this, in the gas sensor 1 of the present invention, an extremely thin gate insulating layer of several nanometers is formed in the ionic liquid IL provided between the carbon nanotube 8 and the gate electrode 7 without using a silicon oxide film such as $SiO_2$, whereby even if the gate voltage $V_g$ of approximately 0.4 [V] is applied to the gate electrode 7, the gas sensor can operate as a transistor, and the gate voltage $V_g$ can be more drastically reduced than in the conventional gas sensors.

Further, since in the gas sensor 1, the gate insulating layer is formed in the ionic liquid IL itself that absorbs a gas, and the change of the state of the gate insulating layer of the ionic liquid IL, which occurs by absorption of the gas is directly reflected in the source-drain current that flows in the carbon nanotube 8, the gas detection sensitivity can be enhanced more than in the conventional gas sensors. Furthermore, since in the gas sensor 1, surface chemical modification does not have to be applied to the carbon nanotube itself as in the conventional gas sensors, and the ionic liquid IL can be simply provided to be in contact with the carbon nanotube 8 and the gate electrode 7, and therefore, the configuration can be simplified correspondingly.

Furthermore, in the gas sensor 1, the source-drain current/gate voltage characteristics change in accordance with the gas concentration in the outside air, and therefore, by measuring the change amount of the source-drain current/gate voltage characteristics, to what extent the gas which is the target of detection is contained in the outside air also can be estimated based on the change amount.

According to the above configuration, by providing the carbon nanotube 8 between the source electrode 3 and the drain electrode 4 in the ionic liquid IL, the change of the state of the electric charges in the ionic liquid IL, which occurs by absorption of a gas is directly reflected in the source-drain current $I_{sd}$ that flows in the carbon nanotube 8, and therefore, the gas detection sensitivity can be enhanced more than in the conventional gas sensors. Further, since the carbon nanotube 8 can be simply provided to be disposed in the ionic liquid IL, the configuration that chemically modifies the surface of the carbon nanotube with a plurality of polymers as in the conventional gas sensors is not necessary, and the configuration can be simplified correspondingly.

Further, since the electric double layer including the gate insulating layer is formed in the ionic liquid IL, and the change of the state of the gate insulating layer in the ionic liquid IL, which occurs by absorption of a gas is directly reflected in the source-drain current $I_{sd}$ that flows in the carbon nanotube 8, and therefore, the gas detection sensitivity can be enhanced more than in the conventional gas sensors. Further, since the ionic liquid IL can be simply provided on the substrate 2 to be in contact with the carbon nanotube 8 and the gate electrode 7, the configuration that chemically modifies the surface of the carbon nanotube with a plurality of polymers as in the conventional gas sensors is not needed, and the configuration can be simplified correspondingly.

(5) Other Embodiments

Figure 22:
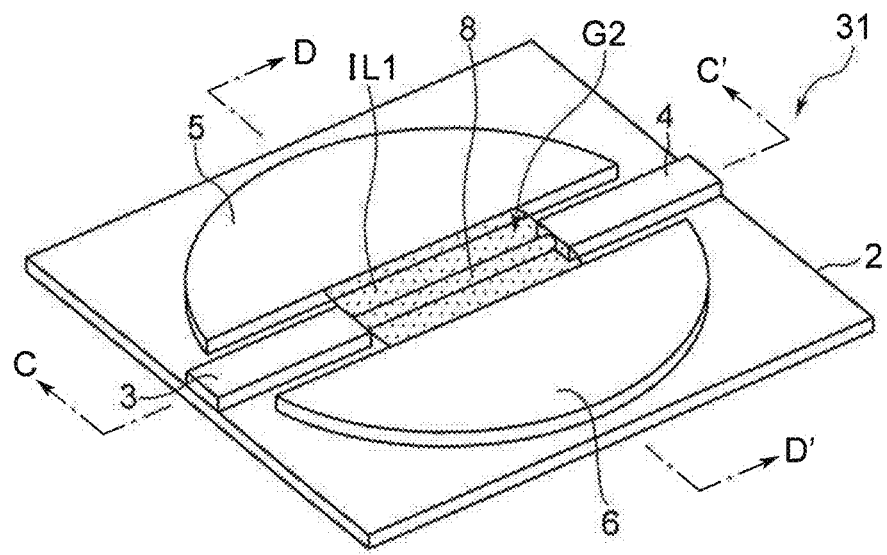
FIG. 22 is a perspective view showing a configuration of a gas sensor (1) according to another embodiment.
Figure 23:
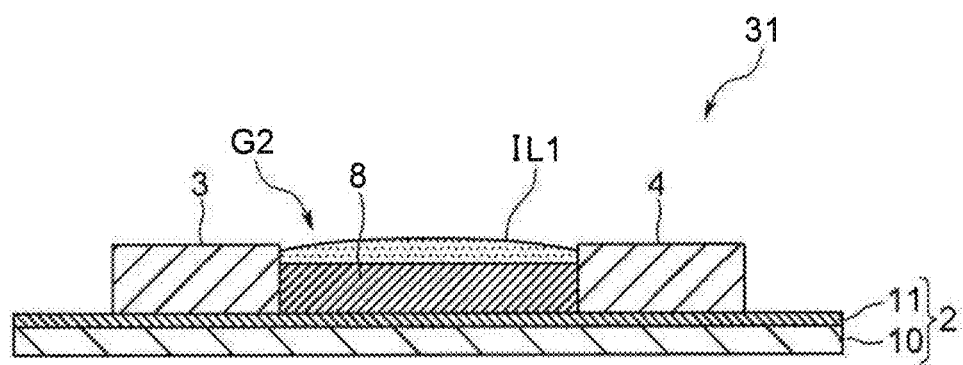
FIG. 23 is a sectional view showing a sectional configuration of a C-C' portion in FIG. 22.
Figure 24:
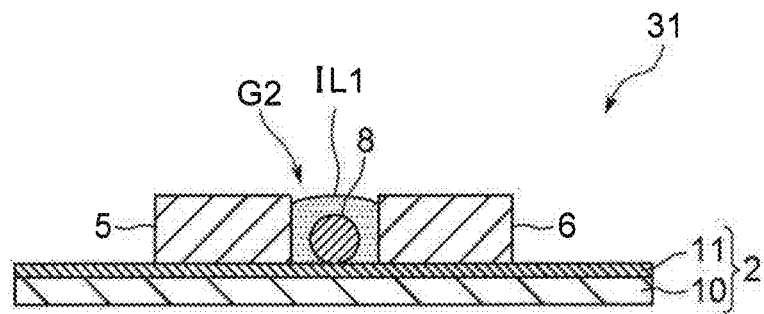
FIG. 24 is a sectional view showing a sectional configuration of a D-D' portion in FIG. 22.

Note that the present invention is not limited to the present embodiment, and can be carried out by being variously modified within the range of the gist of the present invention. In the embodiment described above, the gas sensor 1 is described, in which the ionic liquid IL is provided to be placed not only on the source electrode 3 and the drain electrode 4, but also on the first gate electrode portion 5 and the second gate electrode portion 6, but the present invention is not limited to this. A gas sensor 31 may be applied, in which an ionic liquid IL1 is provided in only a region G2 surrounded by the source electrode 3, the drain electrode 4, the first gate electrode portion 5, and the second gate electrode portion 6 without covering the top surfaces of the source electrode 3, the drain electrode 4, the gate electrode portion 5 and the second gate electrode portion 6, as in FIG. 22 showing the configuration by assigning the components corresponding to those in FIG. 1 with the same reference signs, FIG. 23 showing a sectional configuration of a C-C' portion of FIG. 22, and FIG. 24 showing a sectional configuration of a D-D' portion of FIG. 22.

In practice, since in the gas sensor 31, the ionic liquid IL1 is disposed in the region G2 surrounded by the source electrode 3, the drain electrode 4, the first gate electrode portion 5 and the second gate electrode portion 6 to be in contact with respective side surfaces of the source electrode 3, the drain electrode 4, the first gate electrode portion 5 and the second gate electrode portion 6, miniaturization can be achieved by reducing the amount of the ionic liquid IL1, and the ionic liquid IL1 can be provided on the substrate 2 stably by action of surface tension as well. Further, in the gas sensor 31, an electric double layer including a gate insulating layer of several nanometers is formed in the ionic liquid IL1 when a gate voltage is applied to the ionic liquid IL1 via the gate electrode 7 similarly to the aforementioned embodiment. The ionic liquid IL1 can be reduced to the volume with which the gate insulating layer of approximately several nanometers of the electric double layer can be formed.

Figure 25:
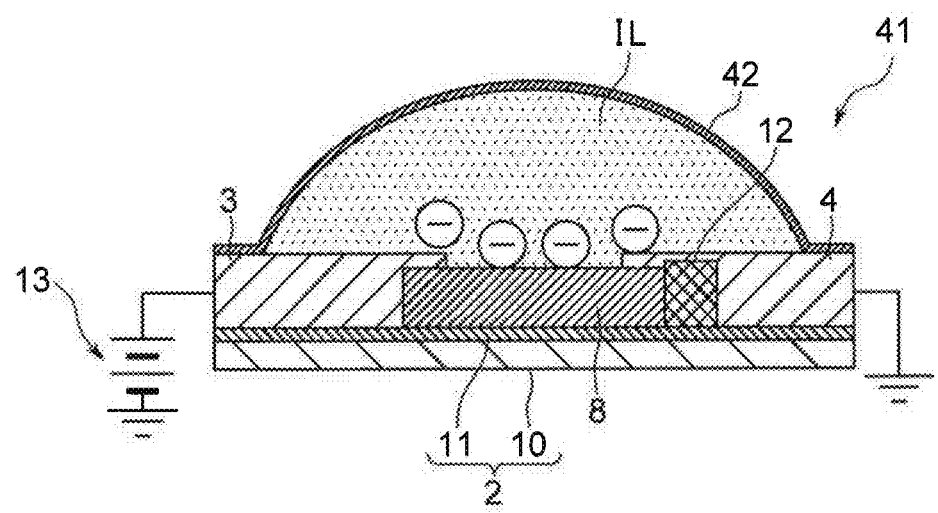
FIG. 25 is a sectional view showing a sectional configuration of a gas sensor (2) according to another embodiment.

Further, in the aforementioned embodiment, the gas sensor 1 in which the ionic liquid IL is simply dropped and placed on the substrate 2 is described, but the present invention is not limited to this. As another embodiment, a gas sensor 41 may be applied, which has a configuration in which a liquid surface of the ionic liquid IL formed in a curved shape is covered with a coating film 42 capable of permeating outside air such as parylene, as in FIG. 25 showing the configuration by assigning the components corresponding to those in FIG. 3 with the same reference signs. In this case, even if an external force is applied to the substrate 2 and the substrate 2 is tilted, the ionic liquid IL can be kept to be held on the substrate 2 stably by the coating film 42 as holding means. Incidentally, the gas sensor 41 can be produced by depositing a coating material capable of permeating outside air such as parylene on the ionic liquid IL by, for example, a CVD (Chemical Vapor Deposition) method, after dropping the ionic liquid IL, and forming the coating film 42 directly onto the ionic liquid IL. Further, the gas sensor 41 also can be produced by forming the coating film 42 on the substrate 2 in advance by a coating material capable of permeating outside air such as parylene, and thereafter injecting the ionic liquid IL into the coating film 42 and sealing the ionic liquid IL.

Since in the gas sensor 41 like this, the ionic liquid IL can be held on the substrate 2 stably by the coating film 42, the substrate 2 can be installed on the ceiling in a room with the ionic liquid IL facing down, for example, and the substrate can be installed with the ionic liquid IL facing in various directions in accordance with service conditions.

Further, in the gas sensor 41 like this, a gas absorbing liquid can be isolated from outside air, and therefore, as the gas absorbing liquid, a volatile liquid such as water also can be used. Note that when water is used as the gas absorbing liquid, the water absorbs a gas, whereby in response to a change of the state of the electric charges in the water, the source-drain current $I_{sd}$ that flows in the carbon nanotube 8 changes, and a similar effect to the embodiment described above can be obtained.

Figure 26:
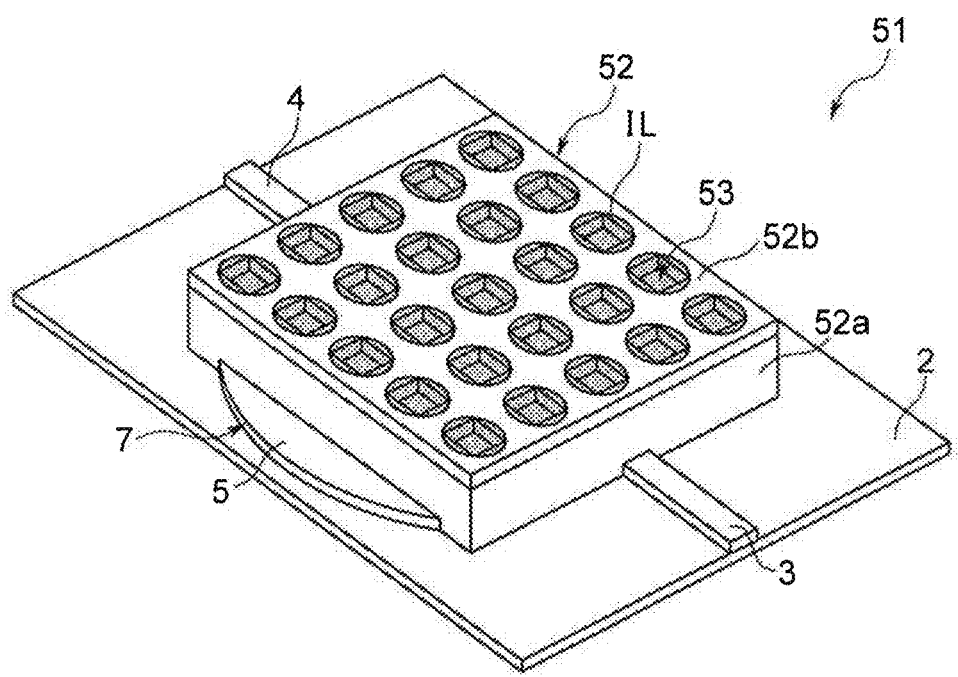
FIG. 26 is a perspective view showing a configuration of a gas sensor (3) according to another embodiment.

Further, as the gas sensor according to another embodiment, as in FIG. 26 showing the configuration by assigning the components corresponding to those in FIG. 1 with the same reference signs, a gas sensor 51 may be applied, which is configured such that a frame body 52 covering the ionic liquid IL is provided on the substrate 2, and the ionic liquid IL is held on the substrate 2 by the frame body 52 as holding means. In this case, the frame body 52 is disposed on the substrate 2 in such a manner as to cover the carbon nanotube 8 (not illustrated) between the source electrode 3 and the drain electrode 4 on the substrate 2, to cover parts of the source electrode 3, the drain electrode 4 and the gate electrode 7 that are disposed around the carbon nanotube 8, and to be able to hold the ionic liquid IL in an internal space.

In practice, the frame body 52 forms the internal space by, for example, a quadrilateral wall portion 52a that holds back the ionic liquid IL, and a plate-shaped top plate portion 52b that is disposed to cover the wall portion 52a, and a plurality of microscopic through-holes 53 that allow the internal space and an outside to communicate with each other are provided by being drilled in the top plate portion 52b. The frame body 52 has a bottom surface portion closed by being installed on the substrate 2, has the internal space communicating with the outside through only the through-holes 53, and can hold the ionic liquid IL in the internal space by the ionic liquid IL being injected into the internal space from the through-holes 53. Here, the frame body 52 is configured to be able to hold the ionic liquid IL reliably, since the surface tension of the ionic liquid IL acts in the through-hole 53 because the through-hole 53 is microscopic, and the ionic liquid IL injected into the internal space hardly flows outside from the through-hole 53.

Further, the ionic liquid IL covers the carbon nanotube in the internal space of the frame body 52, and is also in contact with the first gate electrode portion 5 and the second gate electrode portion 6 (not illustrated) of the gate electrode 7. Thus, with the gas sensor 51, the electric double layer including the gate insulating layer is formed in the ionic liquid IL when the gate voltage is applied to the ionic liquid IL from the gate electrode 7, and a similar effect to the above described embodiment can be provided.

Furthermore, as another embodiment, a configuration may be adopted, in which the substrate 2 provided with the carbon nanotube 8, the gate electrode 7 and the like is installed in a box-shaped storage portion in which the ionic liquid IL is stored, and the substrate 2 is provided in the ionic liquid IL. Such gas sensors with various configurations each with the disposition relation of the substrate 2 and the ionic liquid IL appropriately changed may be applied in accordance with service conditions.

The invention claimed is:

1. A gas sensor that detects a gas that is a target of detection, comprising:
   a carbon nanotube provided between a source electrode and a drain electrode on a substrate, and a source-drain current flows therein; and
   a gas absorbing liquid disposed to cover the carbon nanotube,
   wherein the gas is detected based on a change of the source-drain current in the carbon nanotube caused by absorbing the gas in the gas absorbing liquid,
   wherein the gas absorbing liquid is in contact with the carbon nanotube and a gate electrode on the substrate to become a gate insulating layer, a state of the gate insulating layer changes by absorbing the gas, and the gas is detected based on a change of the source-drain current that occurs in response to the state of the gate insulating layer,
   wherein the gate electrode is configured by a first gate electrode portion and a second gate electrode portion, and the carbon nanotube is disposed between the first gate electrode portion and the second gate electrode portion, and the gas absorbing liquid is disposed to be in contact with the first gate electrode portion and the second gate electrode portion, and
   wherein the gas absorbing liquid is held in a gap formed between the first gate electrode portion and the second gate electrode portion.

2. The gas sensor according to claim 1,
   wherein holding means covering the gas absorbing liquid, and holding the gas absorbing liquid on the substrate is provided.

3. The gas sensor according to claim 1,
   wherein the gas is detected based on a change of a gate voltage of the gate electrode that changes in response to the source-drain current.

4. The gas sensor according to any claim 1,
wherein the gas absorbing liquid is an ionic liquid.

5. The gas sensor according to claim 1, wherein the gas absorbing liquid is a hydroxide aqueous solution of an alkali metal and an alkaline earth metal.

* * * * *